United States Patent
Chen et al.

(10) Patent No.: US 11,690,822 B2
(45) Date of Patent: Jul. 4, 2023

(54) METHOD FOR TREATING NON-COMPACTION CARDIOMYOPATHY

(71) Applicants: Wen-Pin Chen, Taipei (TW); EXCELSIOR PHARMATECH LABS, Taipei (TW)

(72) Inventors: Wen-Pin Chen, Taipei (TW); Mei-Hwan Wu, Taipei (TW); Hong-Nerng Ho, Taipei (TW)

(73) Assignees: EXCELSIOR PHARMATECH LABS, Taipei (TW); NATIONAL TAIWAN UNIVERSITY, Taipei (TW)

( * ) Notice: Subject to any disclaimer, the term of this patent is extended or adjusted under 35 U.S.C. 154(b) by 200 days.

(21) Appl. No.: 15/734,315

(22) PCT Filed: May 23, 2019

(86) PCT No.: PCT/CN2019/088156
§ 371 (c)(1),
(2) Date: Dec. 2, 2020

(87) PCT Pub. No.: WO2019/233285
PCT Pub. Date: Dec. 12, 2019

(65) Prior Publication Data
US 2021/0220327 A1 Jul. 22, 2021

Related U.S. Application Data

(60) Provisional application No. 62/679,968, filed on Jun. 3, 2018.

(51) Int. Cl.
*A61K 31/366* (2006.01)
*A61P 9/04* (2006.01)
*A61K 9/00* (2006.01)

(52) U.S. Cl.
CPC .............. *A61K 31/366* (2013.01); *A61P 9/04* (2018.01); *A61K 9/0024* (2013.01)

(58) Field of Classification Search
CPC ................................ A61K 31/366; A61P 9/04
See application file for complete search history.

(56) References Cited

U.S. PATENT DOCUMENTS 9,974,767 B2  5/2018  Froehner et al.
2016/0296587 A1  10/2016  Macrae et al.

OTHER PUBLICATIONS

International Search Report and Written Opinion for International Application No. PCT/CN2019/088156 dated Aug. 21, 2019, 9 pages.

*Primary Examiner* — Marcos L Sznaidman
(74) *Attorney, Agent, or Firm* — Amin, Turocy & Watson LLP

(57) ABSTRACT

A method for treating a subject suffering from non-compaction cardiomyopathy (NCC), by administering to the subject suffering from NCC a pharmaceutical composition having a therapeutically effective amount of a EZH2 downregulator including the statin.

11 Claims, 16 Drawing Sheets

METHOD FOR TREATING NON-COMPACTION CARDIOMYOPATHY

BACKGROUND OF THE INVENTION

Field of the Invention

The present invention relates to a method for treating a subject suffering from non-compaction cardiomyopathy (NCC), comprising administering to the subject a pharmaceutical composition comprising a therapeutically effective amount of a EZH2 downregulator. In particular, the EZH2 downregulator is able to inhibit EZH2 overexpression induced by pathogenic mutations in NCC and consequently reduces the recruitment of DNA methyltransferase (DNMT) that causes epigenetic alterations. Therefore, the EZH2 downregulator can improve the cardiometabolism and disease progression by recovering the functional gene expressions in left ventricular non-compaction cardiomyopathy (LVNC).

Description of Prior Art

Left ventricular non-compaction cardiomyopathy (LVNC), characterized by a spongy left ventricular (LV) myocardium with abnormal trabeculations particularly in the left ventricular apex, is a distinct cardiomyopathy. According to a population study, the mean annual incidence of newly diagnosed cases was 0.11 per 100,000 children aged <10 years, and was highest in the first year of life (0.83 per 100,000 infants). Only 48% was free from death or transplantation 10 years after diagnosis. Children who usually showed symptoms in early infancy with a predominant dilated phenotype had even worse long-term outcomes. LVNC can present as an isolated condition or associated with congenital heart diseases, neuromuscular diseases or genetic syndromes. Genetic mutations involved in the pathogenesis of LVNC include the mutations in MIB1, TBX20, two calcium handling genes of TAZ and LMNA, NUMB/NUMBL, mitochondrial genome mutations (distal 22q11-2), and the sarcomere-encoding genes (MYH7, ACTC1, TNNT2, MYBPC3, TPM1, LDB3, and TNNI3). Cardiometabolic dysfunction has also been described as part of the pathophysiology of LVNC.

The state-of-the-art therapy for LVNC with heart failure includes anti-congestive medications (diuretics, ACE inhibitors, AT1 receptor blockers and beta-blockers) and antiplatelet therapy to prevent thromboembolism. For those who failed medical control, heart transplant will be considered. In spite of initially improved LV function in some patients, late deterioration would still occur at a median interval of 6.3 years. To improve the poor prognosis of such patients, precision medicine may be effective to provide another strategic approach to identify new treatments.

SUMMARY OF THE INVENTION

The present invention provides a method for treating a subject suffering from non-compaction cardiomyopathy (NCC), comprising administering to the subject suffering from NCC a pharmaceutical composition comprising a therapeutically effective amount of a EZH2 downregulator, such as statins, particularly simvastatin.

BRIEF DESCRIPTION OF THE DRAWINGS

FIG. 2 shows that the epigenetic abnormality in human LVNC cardiomyocytes links to cardiac dysfunction.

Figure 1A:
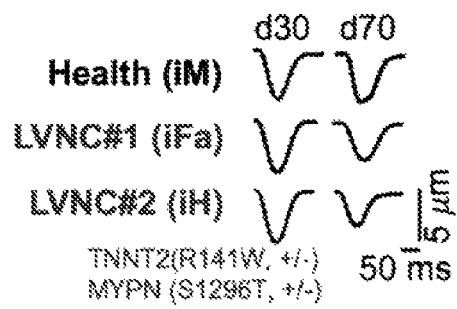
(FIG. 1A) A decrease of cardiomyocyte contraction is observed in human cardiomyocytes derived from patients' hiPSCs of a LVNC family (patients: LVNC #1: iF & LVNC #2: iH) carrying the heterozygous missense mutations in TNNT2 (R141W) and MYPN(S1296T) on day 70 after differentiation in vitro, as compared to those in human cardiomyocytes derived from healthy patient (il).

iH, zeb: LVNC cardiomyocytes treated with Zebularine; iH, gsk: LVNC cardiomyocytes treated with GSK503.

FIG. 3 shows that simvastatin is identified as one of the EZH2 downregulators that can attenuate the abnormal EZH2 overexpression and recover cardiac functions in LVNC cardiomyocytes. (FIG. 3A) Drug repurposing screening finds that simvastatin can selectively normalize EZH2 expression in LVNC cardiomyocytes. (FIG. 3B) Simvastatin (5 µM) can significantly recover cardiac contraction and positive inotropic response to isoprenaline (three doses: 0.03, 0.1, 1 µM)-induced β-stimulation as shown in the min-to-max plot with mean line in the box and the error bar of SEM. At the same concentration of 5 µM, the efficacy of simvastatin is better than those of the other statins, such as lovastatin, atorvastatin and fluvastatin. In addition to the strategy of inhibiting abnormal histone methylation for the recovery of cardiac functional gene expressions, it is further examined whether maintaining the histone acetylated status can also recover gene expressions. It is demonstrated that SAHA (a histone deacetylase (HDAC) inhibitor, 5 µM) is unable to improve LVNC cardiac functions. (FIG. 3C) Simvastatin (5 µM) can prominently improve mitochondrial function of LVNC cardiomyocytes. The effect of simvastatin at low dose (5 µM) in improving cardiac metabolic function is better than that at high dose (10 µM). (FIG. 3D) Simvastatin can recover the expression of mitochondrial respiratory chain genes, such as CYB5R2 and CYBRD1. Zebularine (zeb, 100 µM) can produce similar effect like simvastatin. (FIG. 3E) Simvastatin can dose-dependently recover the expressions of cardiac metabolic genes. Control: LVNC cardiomyocytes without treatment; Simvastatin: LVNC cardiomyocytes treated with simvastatin; SAHA: LVNC cardiomyocytes treated with SAHA; Atorvastatin: LVNC cardiomyocytes treated with atorvastatin; Fluvastatin: LVNC cardiomyocytes treated with fluvastatin; Lovastatin: LVNC cardiomyocytes treated with Lovastatin; iH, ctrl: LVNC cardiomyocytes without treatment; iH, s5: LVNC cardiomyocytes treated with 5 µM simvastatin; iH, s10: LVNC cardiomyocytes treated with 10 µM simvastatin; iH, s: LVNC cardiomyocytes treated with simvastatin; iH, zeb: LVNC cardiomyocytes treated with Zebularine; iM: healthy human cardiomyocyte; iH: LVNC cardiomyocytes.

FIG. 4 shows that simvastatin can maintain the normal cell size of LVNC cardiomyocytes and the expressions of cardiac metabolic and muscular proteins. (FIG. 4A) Simvastatin (5 µM) can inhibit the enlargement of LVNC cardiomyocytes. SA: sarcomeric actinin α; TNNT2: troponin T; DAPI: nuclear counterstain. (FIG. 4B) Hierarchical clustering plot and principal component analysis of the proteomics in LVNC cardiomyocytes treated with or without simvastatin reveal the protein profile in simvastatin-treated group is markedly moving close to that in healthy group. (FIG. 4C) The STRING functional protein interaction network highlights the major recovery of the functional proteins in the intersection of 69 proteins that are highly expressed in both healthy/iH,ctrl and iH,s/iH,ctrl. The recovered proteins involve in the function of muscle contraction, cellular structure, promoter activity and glucose metabolism. (FIG. 4D) The same effect of simvastatin on the protein profiling of LVNC cardiomyocytes between two LVNC patients (iFa & iH) and the function of the proteins are further characterized. There are 27 proteins that are significantly upregulated in both of iF,s/iF,ctrl and iH,s/iH,ctrl. Gene ontology GO enrichment analysis finds that the majority of the protein function includes the top three of the metabolic process, cellular component organization, and biological regulation. iH, ctrl: LVNC cardiomyocytes from iH patient without treatment; iH, s: LVNC cardiomyocytes from iH patient treated with simvastatin; iFa, ctrl: LVNC cardiomyocytes from iFa patient without treatment; iFa, s: LVNC cardiomyocytes from iFa patient treated with simvastatin.

Figure 5A:
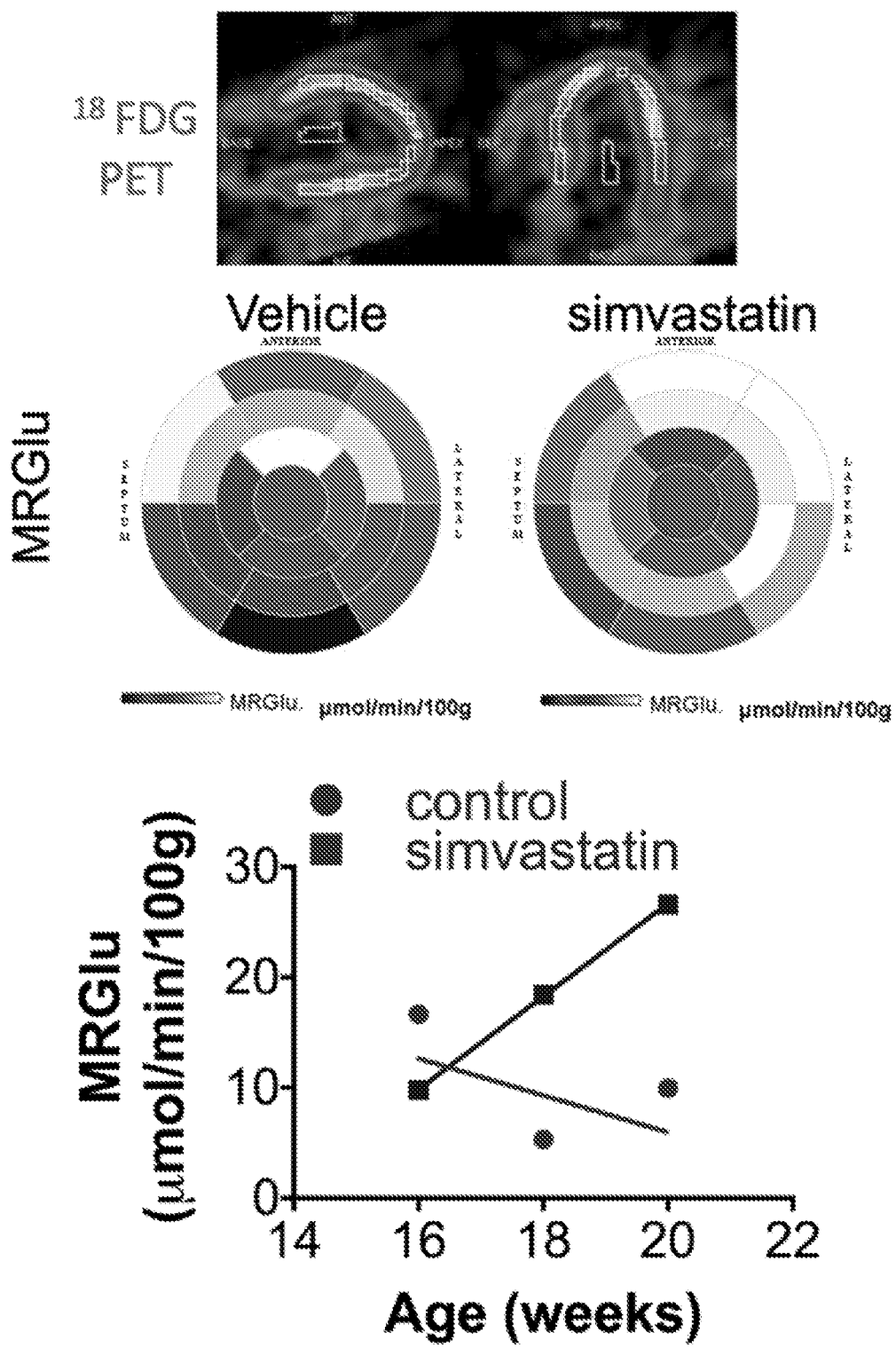
Figure 5B:
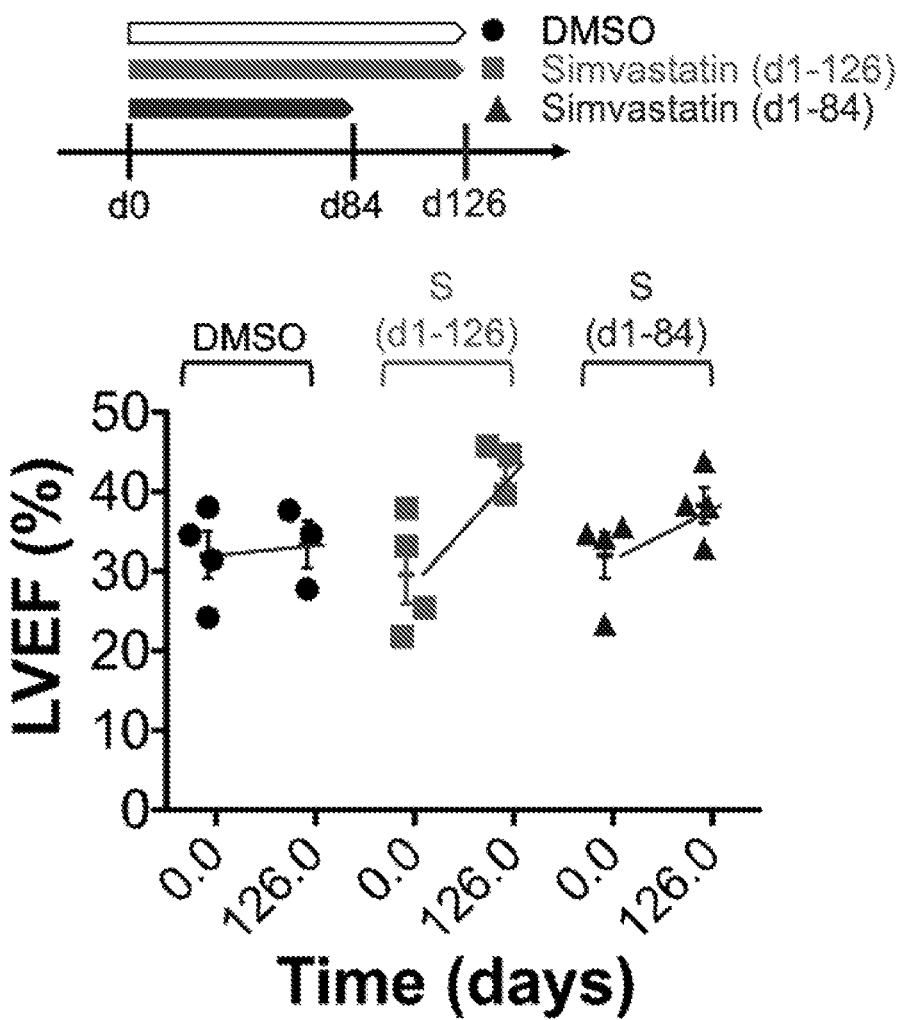

FIG. 5 shows that simvastatin significantly improves cardiometabolism and cardiac function in vivo in the heterozygous ($Tnnt2^{R154W/+}::Mypn^{S1291T/+}$) LVNC mice for the mutations of gene-targeted knock-in Tnnt2 (R154W) and Mypn (S1291T). (FIG. 5A) Dynamic small-animal $^{18}$F-FDG PET scan is conducted to estimate the left ventricular metabolic rate of glucose (MRGlu) in $Tnnt2^{R154W/+}::Mypn^{S1291T/+}$ LVNC mice treated with or without simvastatin. $Tnnt2^{R154W/+}::Mypn^{S1291T/+}$ LVNC mice at different age of 10, 12 and 14 weeks are implanted with the osmotic pump (ALZET Model 2006) to administer simvastatin (3.5 mg/kg/3.6 µL/day, blue square) or DMSO (3.6 µL/day, red circle) for 6 consecutive weeks. Mice are fasted for 16-20 h before the $^{18}$F-FDG PET scan. Cardiac glucose metabolic rate is calculated by Patlak plot corrected with the fasting plasma glucose. Linear regression analysis is performed to obtain the results, Y=−1.667X+39.31 ($R^2$=0.2585, non-zero slope, P=0.4916) in the DMSO vehicle group and Y=4.205X−57.43 ($R^2$=0.9998, non-zero slope, P=0.0095) in the simvastatin group, and there is a significant difference (P=0.0034) in the slopes of MRGlu vs. age between the vehicle- and the simvastatin-groups. (FIG. 5B) Left ventricular ejection fraction (LVEF %) of the LVNC mice treated with vehicle (DMSO, 3.6 L/day) or simvastatin (3.5 mg/kg/3.6 L/day) is measured by echocardiography (VisualSonics Vevo 2100 system) before and on day 126 after the implantation of drug-delivering osmotic pump during 1-84 or 1-126 days as shown in the timeline. The linear regression is performed to determine whether the treatment is effective. In the vehicle DMSO group, it is not significant in the slope deviation from zero (Y=0.01013*X+32.06, P=0.7769, R square=0.01757, n=4). In the continuous simvastatin treatment for 126 days group (S(d1-126), the slope is significantly deviated from zero (Y=0.1098*X+29.55, P=0.0297, R square=0.6445, n=4). In the S(d1-84) group, the LVNC mice are treated with simvastatin during the initial 84 days, and then the drug treatment is stopped (drug holiday) for another 42 days. The slope of cardiac function change in the S(d1-84) group is not significantly deviated from zero (Y=0.05031*X+31.95, P=0.1326, R square=0.3352, n=4). It indicates the continuous low-dose-simvastatin treatment is needed to maintain the good prognosis in LVNC cardiac function. Vehicle: LVNC mice treated with DMSO; Simvastatin: LVNC mice treated with simvastatin; Control: LVNC mice treated with DMSO; DMSO: LVNC mice treated with DMSO.

Figure 6A:
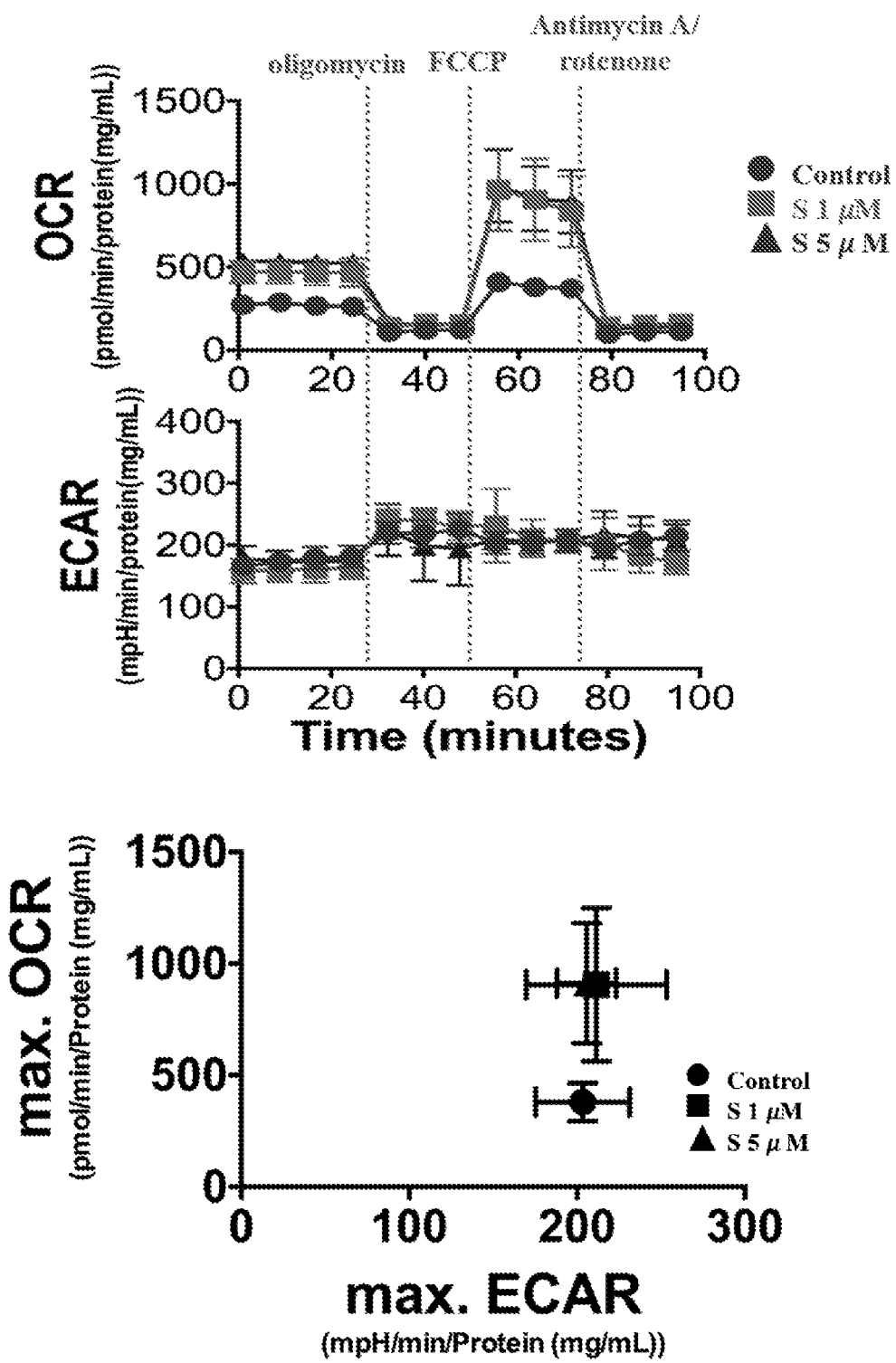
Figure 6B:
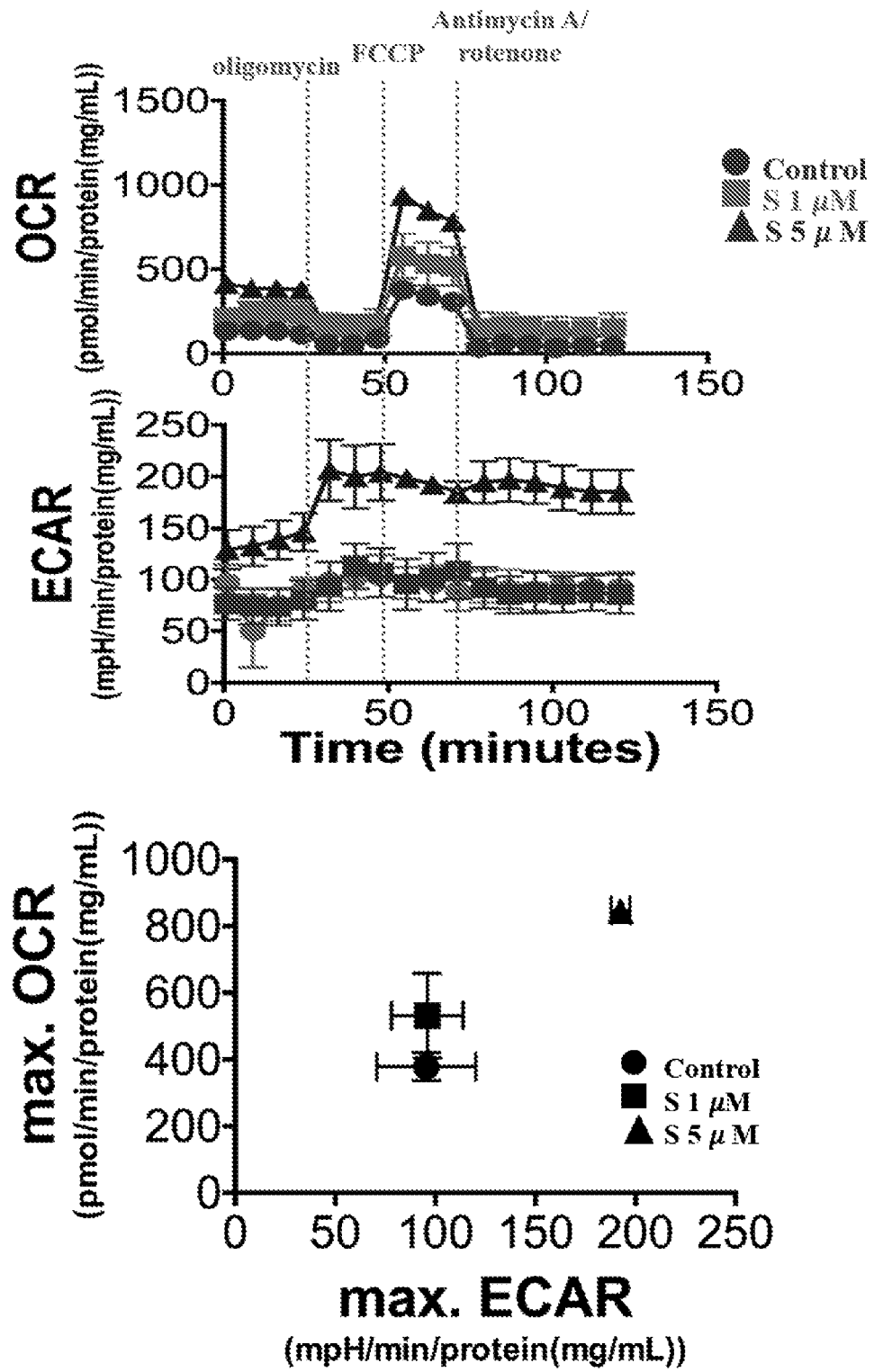

FIG. 6 shows that simvastatin (1-5 µM) can also improve mitochondrial function in LVNC cardiomyocytes derived from the other LVNC patients with complications such as (FIG. 6A) Barth syndrome (TAZ (c.153C>G, NM_000116.4)) and (FIG. 6B) Duchenne/Becker Muscular Dystrophy (DMD (c.10997_10999delCCT, NM_004006.2)). Control: LVNC cardiomyocytes without treatment; S 1 µM: LVNC cardiomyocytes treated with 1 µM simvastatin; S 5 µM: LVNC cardiomyocytes treated with 5 µM simvastatin.

DETAILED DESCRIPTION OF THE INVENTION

The pathogenesis of left ventricle non-compaction (LVNC) is multifactorial. The prognosis of left ventricle non-compaction cardiomyopathy (LVNC) is poor, particularly in those who onset during infancy. Transplant needs to be considered by those who anti-congestive medications fail. The precision medicine is urgently needed by those who onset during infancy due to the unmet medical need and lack of small hearts for transplant. The present invention conducts drug repurposing and screening in human cardiomyocytes derived from LVNC patient's iPSC (LVNC-hiPSC-CMs) to identify safe therapeutic medicines. Furthermore, mutant mouse based on the genetic mutation from the LVNC patients has confirmed in vivo the effects of the identified drug, simvastatin. Such approach provides new therapeutic approach for these LVNC patients with a severe heart failure phenotype.

The present invention finds abnormal overexpression of EZH2 in LVNC cardiomyocytes. Furthermore, the present invention demonstrates that the cardiac function of LVNC cardiomyocytes can be improved by administering simvastatin to downregulate EZH2 expression.

The data of the current study from both the cardiomyocytes derived from human induced pluripotent stem cell (hiPSC-CMs) and the mutant mice provide strong evidence supporting the beneficial effects of simvastatin on the cardiac phenotype, especially in low dose range. The LVNC-hiPSC-CMs recapitulate the cardiac disease phenotype of decreased contractility in vitro on day 70 after differentiation. Simvastatin acts as an EZH2 downregulator to exert a consistent action in improving cardiometabolism to increase mitochondrial ATP production in LVNC-hiPSC-CMs with the treatment from day 30 through day 70. Simvastatin at low dose effectively improves mitochondrial function and preserves the morphology of myocyte in LVNC-hiPSC-CMs. In addition, simvastatin can maintain the normal cell size of LVNC cardiomyocytes and the expressions of cardiac metabolic and muscular genes. In $Tnnt2^{R154W/+}::Mypn^{S1291T/+}$ LVNC mice exhibiting the phenotype of cardiomyopathy, the beneficial effects of simvastatin are further confirmed. In LVNC patients, the lower global myocardial glucose uptake is detected by using the 18F-fluoro-2-deoxyglucose (18F-FDG) dynamic positron emission tomography (PET) examination. In $Tnnt2^{R154W/+}::Mypn^{S1291T/+}$ LVNC mice, a gradual decrease in global myocardial glucose ($^{18}$F-FDG) uptake measured by PET matches the gradual deterioration of cardiac contraction. Simvastatin treatment at low dose increases prominently myocardial glucose uptake, prevents the heart from deteriorating dilation, and recovers cardiac function in LVNC mice.

Simvastatin can also improve mitochondrial function of LVNC cardiomyocytes derived from the other LVNC patients with complications such as Barth syndrome (BS) or Duchenne/Becker Muscular Dystrophy (DMD).

The present invention demonstrates that simvastatin can act as an EZH2 downregulator to ameliorate disease progression and maintain good prognosis in LVNC patients through epigenetic regulation to recover the expressions of those genes involved in cardiometabolism and contractile function. This breakthrough fulfills unmet medical needs for precision medicine in LVNC.

The term "a" or "an" as used herein is to describe elements and ingredients of the present invention. The term is used only for convenience and providing the basic concepts of the present invention. Furthermore, the description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The term "or" as used herein may mean "and/or."

The present invention provides a method for treating a subject suffering from non-compaction cardiomyopathy (NCC), comprising administering to the subject suffering from NCC a pharmaceutical composition comprising a therapeutically effective amount of a EZH2 downregulator.

Non-compaction cardiomyopathy (NCC), also called spongiform cardiomyopathy, is a rare congenital cardiomyopathy that affects both children and adults. It results from the failure of myocardial development during embryogenesis. During development, the majority of heart muscles is a sponge-like meshwork of interwoven myocardial fibers. As normal development progresses, these trabeculated structures undergo significant compaction that transforms them from a spongy-like meshwork to a solid structure. This process is particularly apparent in the ventricles, and particularly so in the left ventricle. Non-compaction cardiomyopathy results when there is a failure of this process of compaction. Because the consequence of non-compaction is particularly evident in the left ventricle, the condition is also called left ventricular non-compaction. In one embodiment of the present invention, the NCC is a left ventricle non-compaction cardiomyopathy (LVNC). In addition, BS or DMD is also accompanied with LVNC. Therefore, in one embodiment, the subject suffers from LVNC with BS or DMD.

As used herein, the term "left ventricle non-compaction cardiomyopathy" or "LVNC" refers to a non-compaction cardiomyopathy (spongiform cardiomyopathy) in which the ventricles, particularly the left ventricle, fails to undergo full compaction. LVNC is caused by mutations in certain genes, e.g., TNNT2, TAZ and DMD.

In one embodiment of the present invention, the symptoms of NCC or LVNC comprise heart failure, ventricular arrhythmias and systemic embolic condition. In another embodiment, the symptoms of NCC or LVNC comprise dilated ventricles, impaired ventricular contractility, larger cardiomyocytes, loss of β-adrenergic responsiveness, abnormal expressions of mitochondrial respiratory chain genes and cardiac metabolism dysfunction.

The present invention demonstrates the overexpression of EZH2 in LVNC cardiomyocytes. Therefore, an EZH2 downregulator is able to inhibit EZH2 overexpression to improve the NCC or LVNC. In particular, the EZH2 downregulator is able to inhibit EZH2 overexpression induced by pathogenic mutations in NCC and consequently reduces the recruitment of DNA methyltransferase (DNMT) that causes epigenetic alterations. Therefore, the EZH2 downregulator can improve the cardiometabolism and disease progression by recovering the functional gene expressions in NCC or LVNC.

In general, the statin is identified as one of the EZH2 downregulators. In one embodiment, the EZH2 downregulator comprises a statin. In a preferred embodiment, low doses of simvastatin can selectively inhibit the overexpression of EHZ2 to recover cardiac metabolism and ventricular function.

The statin can treat or improve the symptoms of NCC or LVNC. In one embodiment, the therapeutically effective amount of the statin is sufficient to treat the NCC or LVNC by improving cardiac functions. In a preferred embodiment, the cardiac functions comprise cardiac metabolism and ventricular function.

Examples of useful statins include, but are not limited to, lovastatin, simvastatin, pravastatin, fluvastatin, atorvastatin, cerivastatin, mevastatin, rosuvastatin and itavastatin. In a preferred embodiment, the statin is selected from the group consisting of lovastatin, simvastatin, pravastatin, fluvastatin, atorvastatin, cerivastatin, mevastatin, rosuvastatin and itavastatin. In a more preferred embodiment, the statin is simvastatin.

The symptoms of NCC or LVNC can be treated by administering an EZH2 downregulator for correcting overexpression of EZH2. Thus, the statin (e.g., simvastatin) can treat a NCC or LVNC patient by downregulating the expression of EZH2. In one embodiment, the therapeutically effective amount of the EZH2 downregulator is sufficient to treat the NCC or LVNC by downregulating the expression of EZH2. In a preferred embodiment, the therapeutically effective amount of the statin is sufficient to treat the NCC or LVNC by downregulating the expression of EZH2. In a more preferred embodiment, the therapeutically effective amount of the simvastatin is sufficient to treat the NCC or LVNC by downregulating the expression of EZH2.

In one embodiment, the cardiac metabolism comprises cardiac fatty acid metabolism, glucose metabolism and mitochondrial respiratory chain. Therefore, the statin improves cardiac metabolism and mitochondrial function. Besides, the cardiac metabolism comprises the β-adrenergic responsiveness. Therefore, the statin also can recover β-adrenergic responsiveness.

The β-adrenergic responsiveness is involved in the production of ATP in mitochondria. The statin can improve the mitochondrial function in the subject suffering from NCC by recovering the expression of mitochondrial respiratory chain genes. In one embodiment, the EZH2 downregulator (e.g., statin) improves the mitochondrial function. In a preferred embodiment, the EZH2 downregulator (e.g., statin) increases mitochondrial ATP production.

In addition, the EZH2 downregulator (e.g., statin or simvastatin) improves or treats the abnormal ventricular function in the LVNC patient. In one embodiment, the EZH2 downregulator (e.g., statin) improves the ventricular function by improving the shortening velocity of the cardiomyocytes, maintaining normal cell size of the cardiomyocytes, and recovering the expressions of muscular proteins. In a preferred embodiment, the muscular proteins comprise tropomyosin, sarcomeric actinin α and troponin T. Therefore, the EZH2 downregulator (e.g., statin) can recover the expression of tropomyosin, sarcomeric actinin α and troponin T.

The symptoms of a dilated ventricle in NCC or LVNC patients can be improved by administrating an EZH2 downregulator (e.g., statin or simvastatin), because the EZH2 downregulator has a function of maintaining the normal cell size of the cardiomyocytes.

As used herein, the term "treating" refers to therapeutic treatments, wherein the subject is to reverse, alleviate, ameliorate, inhibit, slow down or stop the progression or severity of a condition associated with a disease or disorder, e.g., NCC and LVNC. The term "treating" includes reducing or alleviating at least one adverse effect or symptom of a condition, disease or disorder associated with NCC or LVNC. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least a slowdown of, progress or worsening of symptoms compared to what would be expected in the absence of treatment. Beneficial or desired clinical results include, but are not limited to, alleviation of one or more symptom(s), diminishment of the extent of disease, stabilizing (i.e., not worsening) the state of disease, delay or slowing of disease progression, amelioration or palliation of a disease state, remission (whether partial or total), reduced interventions, shortened hospital stays, and/or decreased mortality, whether detectable or undetectable. The term "treatment" of a disease also includes providing relief from the symptoms or side-effects of the disease (including palliative treatment). Treatment in this context does not include or encompass a complete "cure."

In one embodiment, the subject is an animal, preferably a mammal, more preferably a human.

In one embodiment, the pharmaceutical composition can optionally include a carrier, such as a pharmaceutically acceptable carrier. In a preferred embodiment, the pharmaceutical composition further comprises a pharmaceutically acceptable carrier. Pharmaceutically acceptable carriers are determined in part by the particular composition being administered, as well as by the particular method used to administer the composition. Accordingly, there is a wide variety of suitable formulations of the pharmaceutical compositions. Formulations suitable for parenteral administration can be formulated, for example, for intravenous, intramuscular, intradermal, intraperitoneal, and subcutaneous routes. Carriers include aqueous isotonic sterile injection solutions, which can contain antioxidants, buffers, bacteriostatic agent, and solutes that render the formulation isotonic with the blood of the intended recipient, and aqueous and non-aqueous sterile suspensions include suspending agents, solubilizers, thickening agents, stabilizers, preservatives, liposomes, microspheres and emulsions. The term "pharmaceutically acceptable" refers to compounds and compositions which can be administered to mammals without undue toxicity.

The EZH2 downregulator (e.g., statin or simvastatin) and a pharmaceutically acceptable carrier may be administered to a subject through a number of different routes known in the art. In one embodiment, the EZH2 downregulator and a pharmaceutically acceptable carrier are administered externally, intravenously, subcutaneously, topically, orally or by muscle or inhalation. The pharmaceutical composition will be delivered to target sites by the digestive system or the circulatory system.

The term "therapeutically effective amount" used herein is a therapeutic dose which can prevent, decrease, stop or reverse a symptom developed in a subject under specific conditions, or partially, completely alleviates symptoms already exist under specific conditions when the subject begins receiving the treatment.

In one embodiment, the therapeutically effective amount of the EZH2 downregulator ranges from 0.01 mg/kg/day to 10 mg/kg/day. In a preferred embodiment, the therapeutically effective amount of the EZH2 downregulator ranges from 0.05 mg/kg/day to 5 mg/kg/day. In a more preferred embodiment, the therapeutically effective amount of the EZH2 downregulator ranges from 0.1 mg/kg/day to 1 mg/kg/day.

In another embodiment, the therapeutically effective amount of the statin ranges from 0.01 mg/kg/day to 10 mg/kg/day. In a preferred embodiment, the therapeutically effective amount of the statin ranges from 0.05 mg/kg/day to 5 mg/kg/day. In a more preferred embodiment, the therapeutically effective amount of the statin ranges from 0.1 mg/kg/day to 1 mg/kg/day.

Simvastatin has the best therapeutic efficacy among the statins. Low doses of simvastatin are effective. In another embodiment, the therapeutically effective amount of the simvastatin ranges from 0.01 mg/kg/day to 10 mg/kg/day. In a preferred embodiment, the therapeutically effective amount of the simvastatin ranges from 0.05 mg/kg/day to 5 mg/kg/day. In a more preferred embodiment, the therapeutically effective amount of the simvastatin ranges from 0.1 mg/kg/day to 1 mg/kg/day.

In one embodiment, the EZH2 downregulator is continuously administered to the subject daily with the therapeutic dose to maintain a good prognosis of either the improved ventricular function or the decrease of plasma NT-proBNP. In a preferred embodiment, the statin is administered to the subject daily for at least one year with the therapeutic dose. In a preferred embodiment, the EZH2 downregulator is administered to the subject daily for at least 24 weeks with the therapeutic doses titrated from low doses. In another embodiment, the statin is administered to the subject daily for at least 4 weeks starting from a low dose (0.1 mg/kg/day) and the dose-titration is based on the parameters of ventricular function and plasma NT-proBNP monitored every 4 weeks.

The present invention provides a use of a composition for preparing a drug for treating non-compaction cardiomyopathy (NCC), wherein the composition comprises a EZH2 downregulator.

In one embodiment, the NCC is left ventricle non-compaction cardiomyopathy (LVNC). Barth syndrome (BS) or Duchenne/Becker Muscular Dystrophy (DMD) may be also accompanied with LVNC.

The cause of NCC or LVNC comprises EZH2 overexpression induced by pathogenic mutations. Therefore, the EZH2 downregulator is able to inhibit EZH2 overexpression to improve the NCC or LVNC. The statin is identified as one of the EZH2 downregulators. In one embodiment, the EZH2 downregulator comprises a statin.

Therefore, the EZH2 downregulator (e.g., statin) can treat the symptoms of NCC or LVNC. In one embodiment, the EZH2 downregulator improves the cardiac functions of a subject suffering from NCC or LVNC to treat NCC or LVNC. In a preferred embodiment, the statin improves the cardiac functions of a subject suffering from NCC or LVNC to treat NCC or LVNC. In a more preferred embodiment, the cardiac functions comprise cardiac metabolism and ventricular function.

In another embodiment, the statin comprises lovastatin, simvastatin, pravastatin, fluvastatin, atorvastatin, cerivastatin, mevastatin, rosuvastatin and itavastatin. In a preferred embodiment, the statin comprises atorvastatin and fluvastatin, lovastatin and simvastatin. In a more preferred embodiment, the statin is simvastatin.

Simvastatin acts as an EZH2 downregulator. Therefore, the simvastatin can treat a NCC or LVNC patient by downregulating the expression of EZH2. In one embodiment, the EZH2 downregulator treats the NCC or LVNC by downregulating the expression of EZH2. In a preferred embodiment, the statin treats the NCC or LVNC by downregulating the expression of EZH2. In a more preferred embodiment, the simvastatin treats the NCC or LVNC by downregulating the expression of EZH2.

In one embodiment, the cardiac metabolism comprises cardiac fatty acid metabolism, glucose metabolism and mitochondrial respiratory chain. Therefore, the statin improves cardiac metabolism and mitochondrial function. Besides, the cardiac metabolism comprises the β-adrenergic responsiveness. Therefore, the statin also can recover β-adrenergic responsiveness.

In addition, the EZH2 downregulator (e.g., statin) can improve the mitochondrial function in the subject suffering from NCC by recovering the expression of mitochondrial respiratory chain genes. In one embodiment, the EZH2 downregulator (e.g., statin) improves the mitochondrial function. In a preferred embodiment, the EZH2 downregulator (e.g., statin) increases mitochondrial ATP production.

The EZH2 downregulator (e.g., statin or simvastatin) can improve or treat the abnormal ventricular function of a subject suffering from NCC or LVNC. In one embodiment, the EZH2 downregulator (e.g., statin) improves the ventricular function by improving the shortening velocity of the cardiomyocytes, maintaining the normal cell size of the cardiomyocytes, and recovering the expressions of the muscular proteins. In a preferred embodiment, the muscular proteins comprise tropomyosin, sarcomeric actinin α and troponin T. Therefore, the statin can increase the amount of tropomyosin, sarcomeric actinin a and troponin T.

In one embodiment, the composition is a pharmaceutical composition. In a preferred embodiment, the pharmaceutical composition further comprises a pharmaceutically acceptable carrier. The pharmaceutical composition will be delivered to target sites by the digestive system or the circulatory system.

In one embodiment, the therapeutically effective amount of the EZH2 downregulator ranges from 0.01 mg/kg/day to 10 mg/kg/day. In a preferred embodiment, the therapeutically effective amount of the EZH2 downregulator ranges from 0.05 mg/kg/day to 5 mg/kg/day. In a more preferred embodiment, the therapeutically effective amount of the EZH2 downregulator ranges from 0.1 mg/kg/day to 1 mg/kg/day.

In another embodiment, the therapeutically effective amount of the statin ranges from 0.01 mg/kg/day to 10 mg/kg/day. In a preferred embodiment, the therapeutically effective amount of the statin ranges from 0.05 mg/kg/day to 5 mg/kg/day. In a more preferred embodiment, the therapeutically effective amount of the statin ranges from 0.1 mg/kg/day to 1 mg/kg/day.

Low doses of simvastatin are effective. In another embodiment, the therapeutically effective amount of the simvastatin ranges from 0.01 mg/kg/day to 10 mg/kg/day. In a preferred embodiment, the therapeutically effective amount of the simvastatin ranges from 0.05 mg/kg/day to 5 mg/kg/day. In a more preferred embodiment, the therapeutically effective amount of the simvastatin ranges from 0.1 mg/kg/day to 1 mg/kg/day.

In one embodiment, the EZH2 downregulator is continuously administered to the subject daily with the therapeutic dose to maintain a good prognosis in either the improved ventricular function or the decrease of plasma NT-proBNP. In a preferred embodiment, the statin is administered to the subject daily for at least one year with the therapeutic dose. In a preferred embodiment, the EZH2 downregulator is administered to the subject daily for at least 24 weeks with the therapeutic doses titrated from low doses. In another embodiment, the statin is administered to the subject daily for at least 4 weeks starting from a low dose (0.1 mg/kg/day) and the dose-titration is based on the parameters of ventricular function and plasma NT-proBNP monitored every 4 weeks.

Examples

The examples below are non-limiting and are merely representative of various aspects and features of the present invention.

Methods hiPSC Study

Human induced pluripotent stem cell (hiPSC) lines respectively derived from patients with left ventricular non-compaction cardiomyopathy (LVNC) and a normal healthy woman were reprogrammed through two approaches; one line of each patient was reprogrammed from skin cells by lentivirus carrying four Yamanaka factors (Klf4, Myc, Sox2, Oct4; conducted by Dr. Hong-Nerng Ho at NTU) and the other line was reprogrammed from peripheral blood monocytes (PBMC) by Sendai virus carrying the four Yamanaka factors (conducted by Dr. Joseph C. Wu at Stanford University). Patients consented to collect patients' tissues/blood cells for genetic examination, reprogramming to hiPSC, and pharmacological studies. Drug effect was validated via testing the same drug at the same dose in human cardiomyocytes derived from the two lines of the same patient with at least three independent repeats in each line. Cell shortening was measured by the Ionoptix system (Westwood, Mass., USA), and mitochondrial function was assessed by an Agilent seahorse analyzer (Seahorse Bioscience, MA, USA).

Measurement of Mitochondrial Function

Seahorse assay was performed on day 70 to measure mitochondrial OCR (Oxygen Consumption Rate) and ECAR (Extracellular Acidification Rate) under the conditions in the sequential adding of the XF mito stress test kit with the indicated reagents by the arrows. The data were normalized with total cell proteins in each well. The relationship of OCR vs. ECAR was measured under the conditions of basal (before oligomycin) and maximum respiratory capacity (after FCCP).

Omics Study

Proteomic Analysis

The total proteins of hiPSC-derived cardiomyocytes treated with or without simvastatin were extracted by RIPA buffer containing protease and phosphatase inhibitor cocktails (Thermo Fisher Scientific Inc., USA). The samples were further digested by trypsin. After being desalted and dried, LC-MS/MS analysis was performed by the LTQ-Orbitrap Velos mass spectrometer system. The peptide and protein group IDs were obtained by MASCOT database searching with precursor mass accuracy of 7 ppm and MS/MS accuracy of 0.5 Da. The large mass-spectrometric raw data were further analyzed by the MaxQuant software based on the Uniprot human database with a label-free quantification method and followed by the statistical analysis using the Perseus software.

Transcriptome Analysis

The total RNAs of hiPSCs derived cardiomyocytes treated with or without simvastatin were extracted by TRIzol reagent (Invitrogen, Thermo Fisher Scientific Inc., USA). The total RNAs were further purified from the upper aqueous layer of the TRIzol-chloroform homogenate by the Quick-RNA kit (Zymol Research, CA, USA). TruSeq Stranded mRNA sequencing was performed by Phalanx Biotech. Briefly, polyA mRNA from an input of 500 ng high quality total RNA (RIN value >8) was purified, fragmented, and first- and second-strand cDNA were synthesized. Barcoded linkers were ligated to generate indexed libraries. The libraries were quantified using the Promega QuantiFluor dsDNA System on a Quantus Fluorometer (Promega, Madison, Wis.). The size and purity of the libraries were analyzed using the High Sensitivity D1000 Screen Tape on an Agilent 2200 TapeStation instrument. The libraries were pooled and run on an Illumina HiSeq 2500 sequencer using paired end 100 bp Rapid Run format to generate 40 million total reads per sample. After sequencing, raw reads trimmed to remove low quality base were used in sequencing by Trimmomatic. The following criteria were also applied for raw data cleansing: (1) Cut off when the average quality of sliding window (4-base wide) dropped below 15; and (2) Reads shorter than 35 bp were discarded. After the reads were aligned to the genome, Cuffquant was used on the resulting alignment files to compute the gene and transcript expression profiles. Cuffdiff, a part of the Cufflinks package, took the expression profiles and merged assemblies from two or more conditions to estimate the expression levels by calculating the number of RNA-Seq Fragments Per Kilobase of transcript per total Million (FPKM) fragments mapped. Cuffdiff tested the statistical significance of observed changes and identified genes that were differentially regulated at the transcriptional or post-transcriptional level. Cross-omics data were further analyzed by the Perseus software by joining the data of proteome and transcriptome into one Perseus matrix. Both omics columns were sorted and transformed into ranks. A bivariant test was performed on each annotation term. Gene ontology (GO) enrichment analysis was performed to interpret sets of the genes with the functional characterization based on GO system of the classification. The potential interactions between the molecules were predicted by STRING.

Absolute Quantitative Real-Time PCR

The difference in the gene expressions of the cardiomyocyte treated with or without simvastatin was confirmed by the absolute quantification method with Illumina Eco real-time PCR system. Briefly, following reverse transcription of the extracted mRNA, the template cDNA was mixed with the primers of the interested gene in OmiGreen buffer to run PCR with the standards of five 10-fold serial dilutions covering the range of the unknown sample. The expression of 18S RNA in each sample was also quantified as an internal control.

LVNC Mouse Model and the Cardiac Function Imaging

Tnnt2(R154W)- and Mypn(S1291T)-knockin mice on C57BL/6j background were generated by Gene Knockout Mouse Core Laboratory of National Taiwan University Center of Genomic Medicine. Genetically heterozygous LVNC mice (Tnnt2(R154W)$^{+/-}$:: Mypn(S1291T)$^{+/-}$) were obtained from crossing Tnnt2(R154W)$^{+/-}$ and Mypn(S1291T)$^{+/-}$ mice. PCR and DNA sequencing were performed to confirm the genotype. All animal procedures and protocols were approved by AAALAC-accredited facility.

The cardiac motion function of LVNC mice was measured through echocardiography in M-mode by the VisualSonic vevo 2100 imaging system (VisualSonic Inc., Toronto, Canada). Cardiac glucose metabolic rate of LVNC mice was measured by dynamic small animal positron emission tomography (PET) observation under anesthetization by 2% isoflurane inhalation. $^{18}$F-FDG (fluorodeoxyglucose 18F) uptake in LVNC mouse heart was measured for the analysis of cardiac glucose metabolic rate (MRGlu) by dynamic small animal positron emission tomography (PET) to examine the changes in cardiometabolism.

Statistical Analysis

Repeated measures two-way ANOVA with multiple comparisons by the Tukey test was used to distinguish the difference in cell shortening velocity between DMSO- and simvastatin-groups on day 50 and day 70 in LVNC-hiPSC-CMs of iFa and iH. Linear regression analysis was performed to clarify the difference in the inotropic response to β-adrenergic stimulation in LVNC-hiPSC-CMs, and the change of LVEF or cardiac metabolic rate of glucose in LVNC mice between DMSO vehicle- and simvastatin-groups.

Results

Patient Characteristics and Genetic Information

The patient (iH) was admitted to the institution at 6 months of age due to poor activity for one week. Initial evaluation revealed poor perfusion, hepatomegaly and cardiomegaly, and markedly elevated NT-proBNP (>35000 pg/mL). Echocardiogram under inotropic support showed a dilated left ventricle (LV) (the Z score of LV end-diastolic diameter, 4.7) with impaired LV contractility (LV ejection fraction, 30.3%). Computerized tomography showed normal coronary arteries, a dilated LV with poor LV contractility and non-compaction. Myocarditis survey was negative. Dilated cardiomyopathy with LV non-compaction was diagnosed. General condition improved gradually, though a difficulty in weaning milrinone at the lose dosage range was observed. The patient (iH) was discharged 42 days after admission. Family screening identified that the father (iFa) of the patient (iH) also had a dilated LV and low LV ejection fraction.

Genetic examination of the first LVNC family found that the patient (iH)) and the father (iFa) of the patient (iH) had heterogeneous missense mutation in TNNT2(R141W) and MYPN(S1296T). Homologous mutation in TAZ (Y51*) was found in the second LVNC family with BS, and heterogeneous mutation in DMD (S3666del) with DMD was found in the third LVNC family with DMD.

During the subsequent follow-up, the patient (iH) received medication, including digoxin, furosemide, captopril, carvedilol and aspirin. About 2 years after the disease onset, the growth of the patient (iH) was slow and the body weight was below the 3rd percentile, but the developmental milestones were within normal limits. The LV ejection fraction by echocardiography remained poor and was in the range between 17.5% and 24.5%. The NT-proBNP was between 920 and 1200 pg/ml. The father (iFa) of the patient (iH) also received carvedilol, losartan and aspirin and his cardiac status remained stationary.

Drug Repurposing from LVNC-hiPSC-Derived Cardiomyocytes.

Figure 1B:
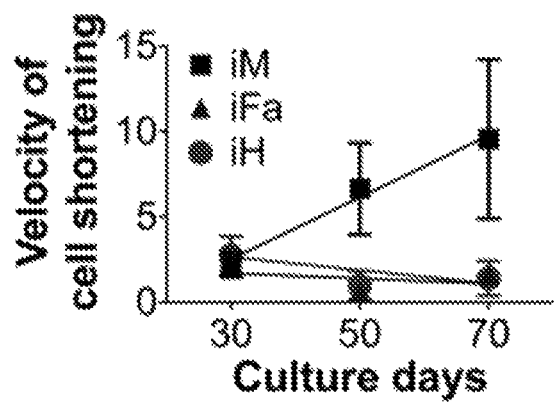
(FIG. 1B) The cell shortening velocity is markedly increased in healthy human cardiomyocytes (iM) during myocyte maturation (day 30-day 70), but is gradually decreased in LVNC patients' cardiomyocytes (iFa & iH). (FIG. C) LVNC patients' cardiomyocytes (iFa & iH) lose positive inotropic response to isoprenaline (a β-adrenoceptor agonist) in vitro.
Figure 1C:
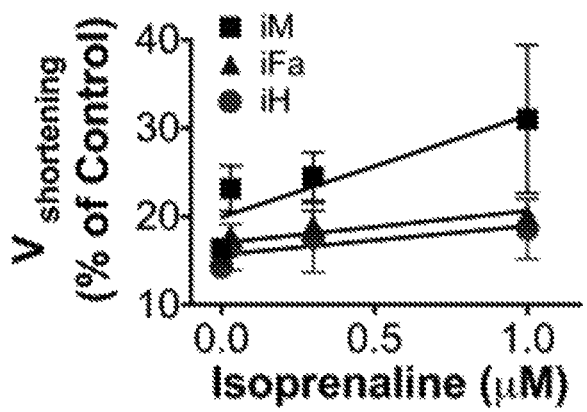
FIG. 1 shows genetic and functional characterization of human LVNC cardiomyocytes.
(FIG. 1D) A decrease of mitochondrial respiratory function is found in LVNC cardiomyocytes (iH) as compared to that in healthy group (iM). OCR indicates the oxygen consumption rate, and ECAR indicates extracellular acidification rate. OCR measures the mitochondrial respiration rate. ECAR measures the glycolysis rate. FCCP: Carbonyl cyanide 4-(trifluoromethoxy) phenylhydrazone.
(FIG. 1E) In LVNC cardiomyocytes, omics analysis (including transcriptome (T) by RNA-sequencing and proteome (P) by LC-MS/MS) reveal a robust gene/protein pattern consistent with suppression of mitochondrial respiratory chain and metabolic process (including (1) GOBP (Gene Ontology Biological Process): glucose metabolic process (T: cluster [3] & P: cluster [1]), (2) GOCC (Gene Ontology Cellular Component): actin filament bundle (T: cluster [6] & P: cluster [6]), (3) GOBP: muscle contraction (T: cluster [8] & P: cluster [4])), in association with the upregulation of certain epigenetic regulators and structure genes (including GOBP: chromatin organization (T: cluster [4] & P: cluster [10]) and GOBP: actin filament bundle (T: cluster [7] & P: cluster [2])) in LVNC cardiomyocytes.
(FIG. 1F) 2D-enrichment analysis finds abnormal expressions of the functional genes involved in muscle contraction (upper panel) and mitochondrial respiratory chain (lower panel) in LVNC cardiomyocytes. H: healthy control; iH: LVNC #2 control.
Figure 1D:
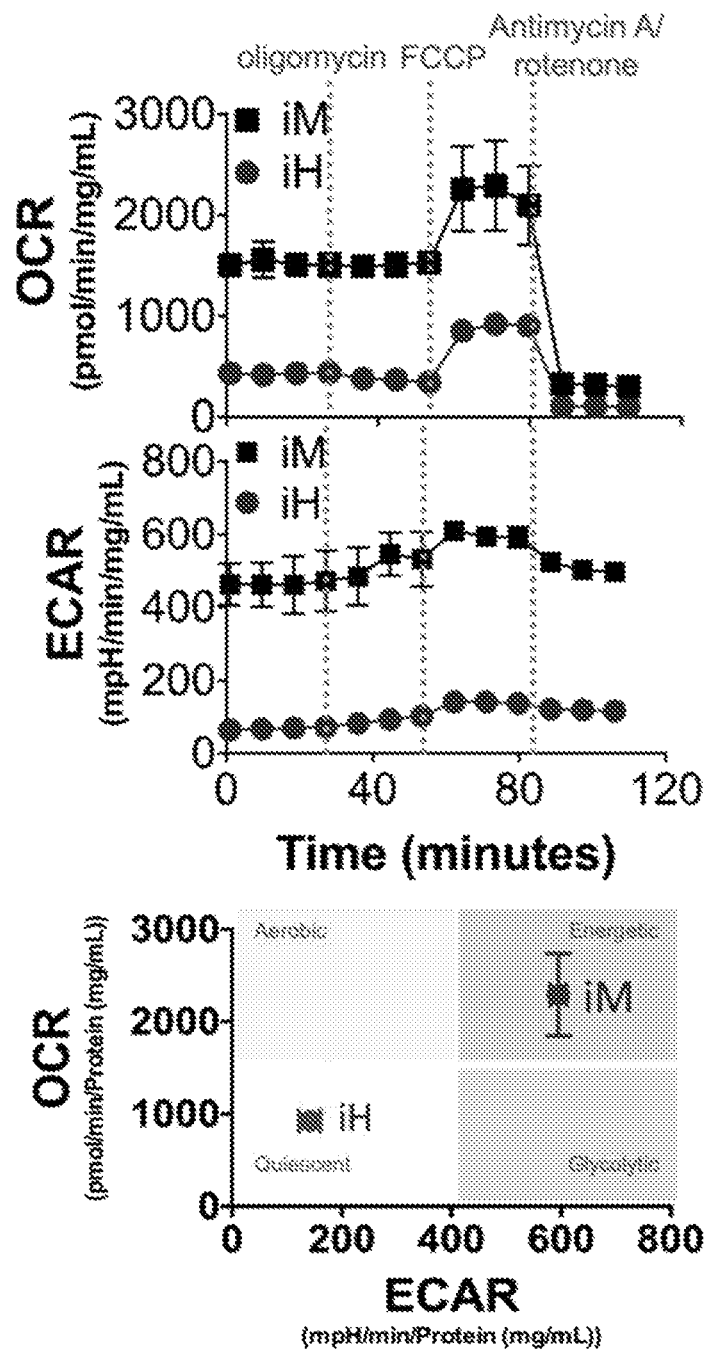
Figure 1E:
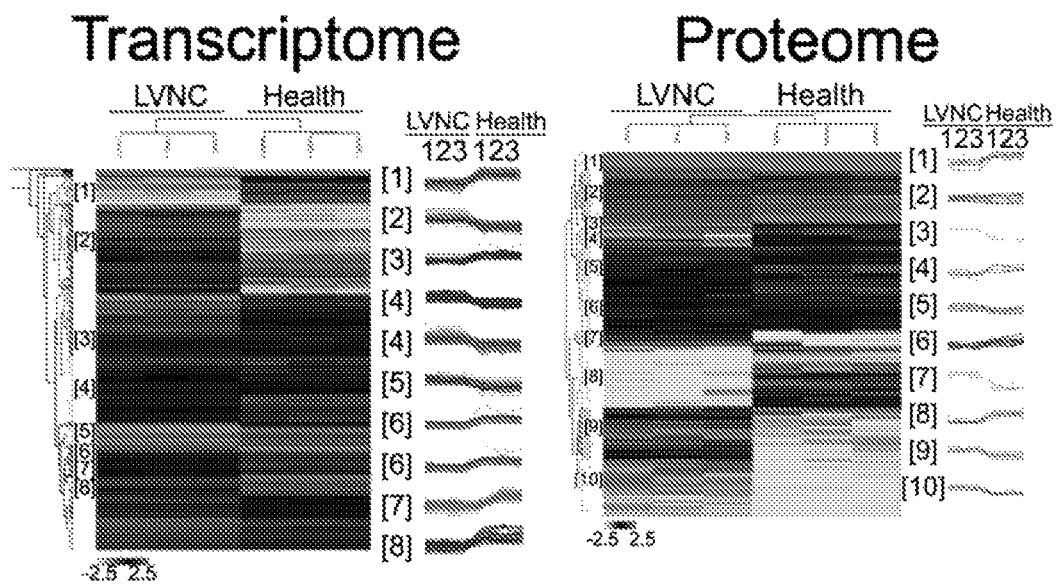
Figure 1F:
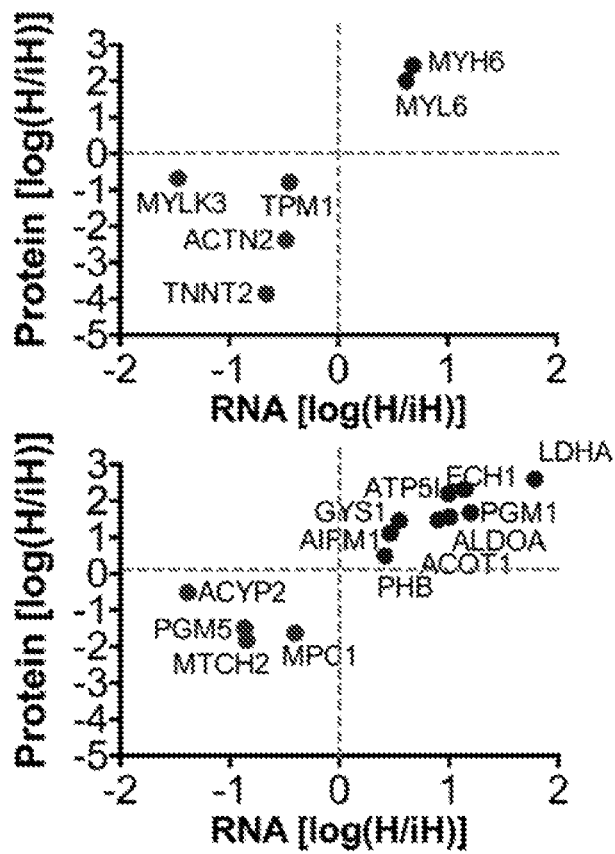
Figure 2A:
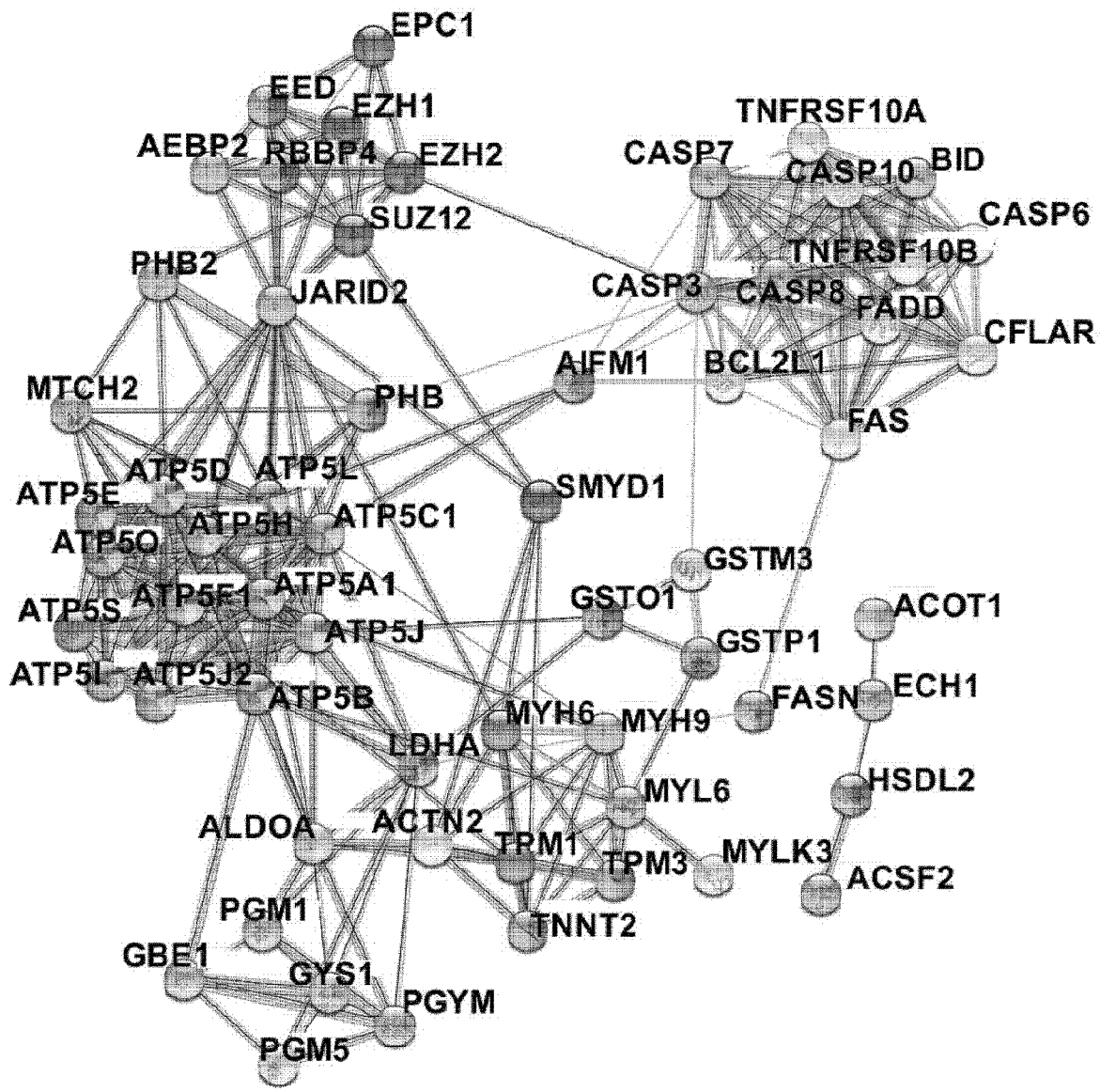
(FIG. 2A) STRING functional protein interaction network is constructed by the significantly changed molecules from the omics analysis in FIGS. 1E-1F. SMYDJ is related to the regulation of muscular gene expressions. Epigenetic regulators PCR2 (including EZH2/SUZ12/EPC1) are involved in regulating the gene expression of mitochondrial respiratory chain and metabolic process.
Figure 2B:
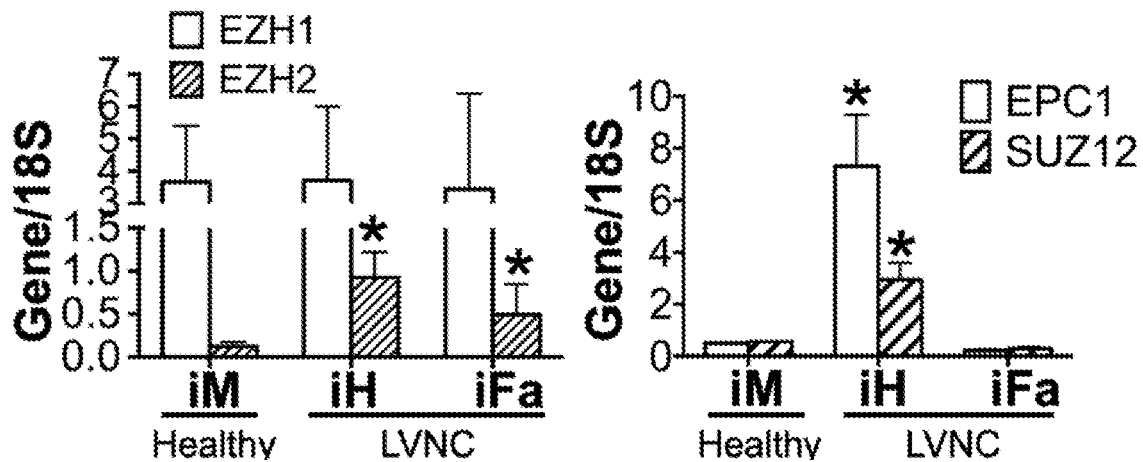
(FIG. 2B) Absolute quantification of real-time PCR is performed to validate the expression of epigenetic regulators. 18S is used as the internal loading control. The significant increase of EZH2 expression is found in iFa- and iH-LVNC cardiomyocytes. EZH2 can act as a methyltransferase or can recruit other DNA methyltransferases (DNMTs) to produce epigenetic modification.
Figure 2C:
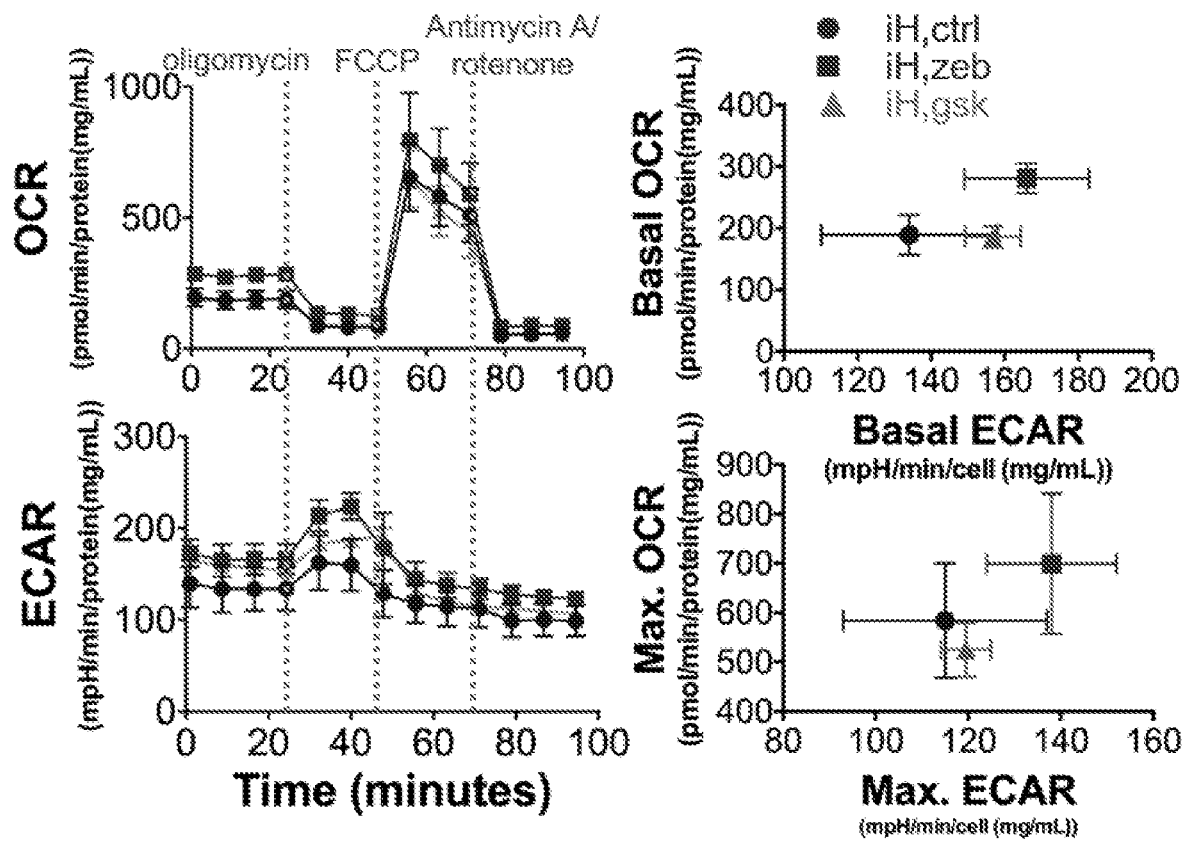
(FIG. 2C) Zebularine (zeb, a DNMT inhibitor, 50 μM) can improve OCR and ECAR of LVNC cardiomyiocytes. GSK503 (gsk, an EZH2 methyltransferase inhibitor, 5 μM) does not significantly improve OCR or ECAR of LVNC cardiomyocytes. These results indicate that it is not the EZH2 methyltransferase but the EZH2-recruited DNMT mediates the abnormal epigenetic action in LVNC. Therefore, inhibiting the abnormal upregulation of EZH2 by EZH2-downregulators in LVNC myocytes, rather than directly inhibiting EZH2 methyltransferase activity, should be the unique therapeutic strategy to normalize cardiac epigenetics by reducing the recruitment of DNMT. EZH2-downregulators can recover cardiac function of LVNC cardiomyocytes with the benefit of the disease-state-specific action. iH,ctrl: LVNC cardiomyocytes without treatment.
Figure 3A:
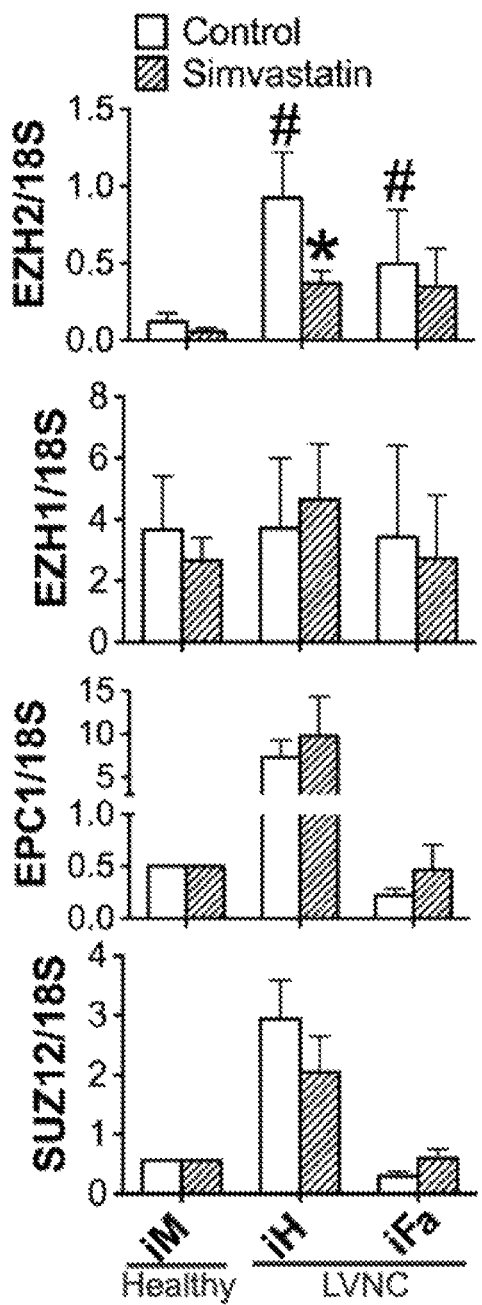
Figure 3B:
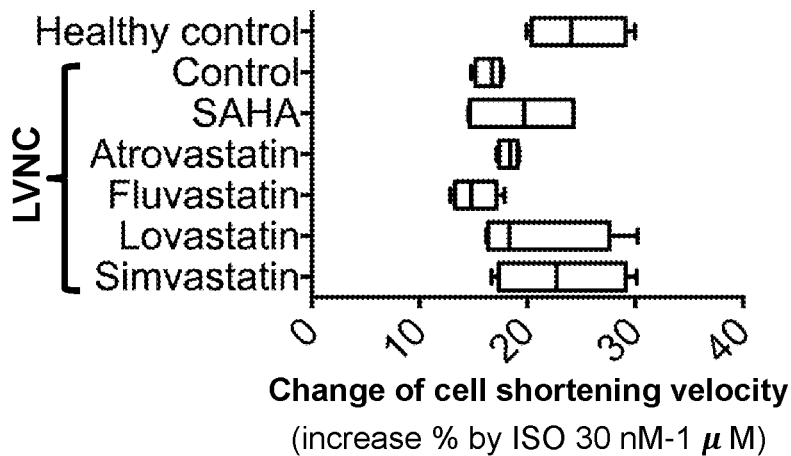
Figure 3C:
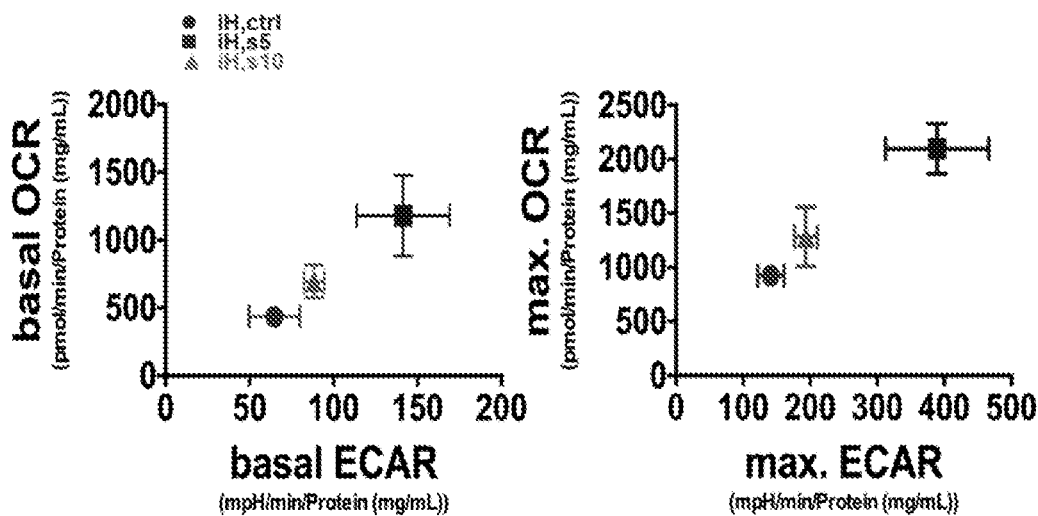
Figure 3D:
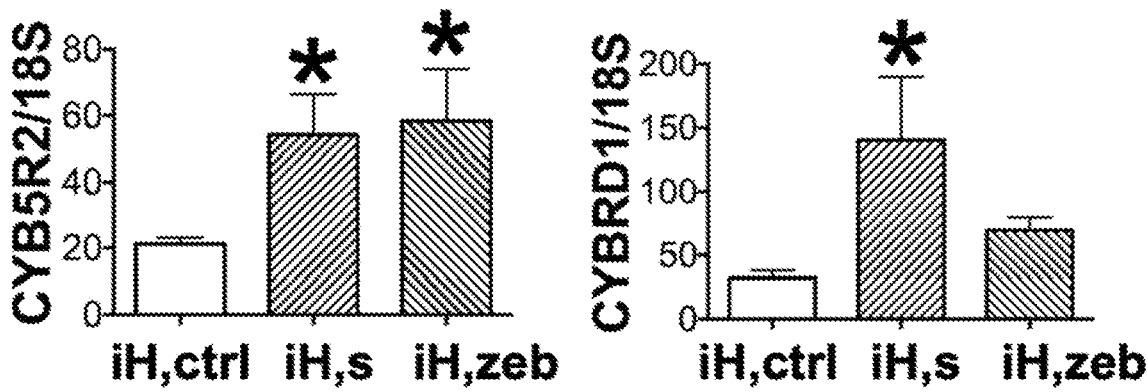
Figure 3E:
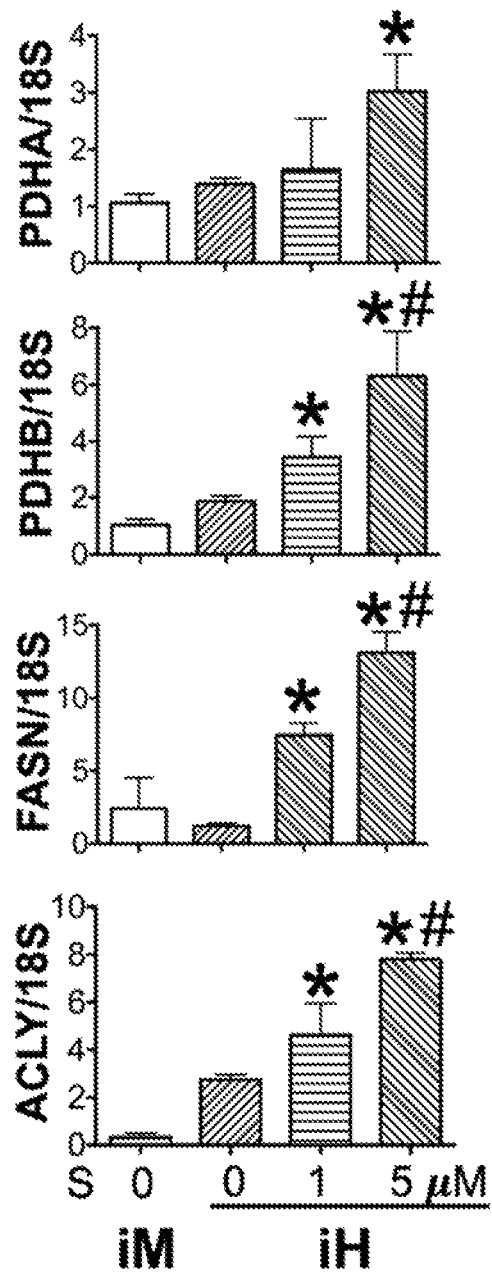
Figure 4A:
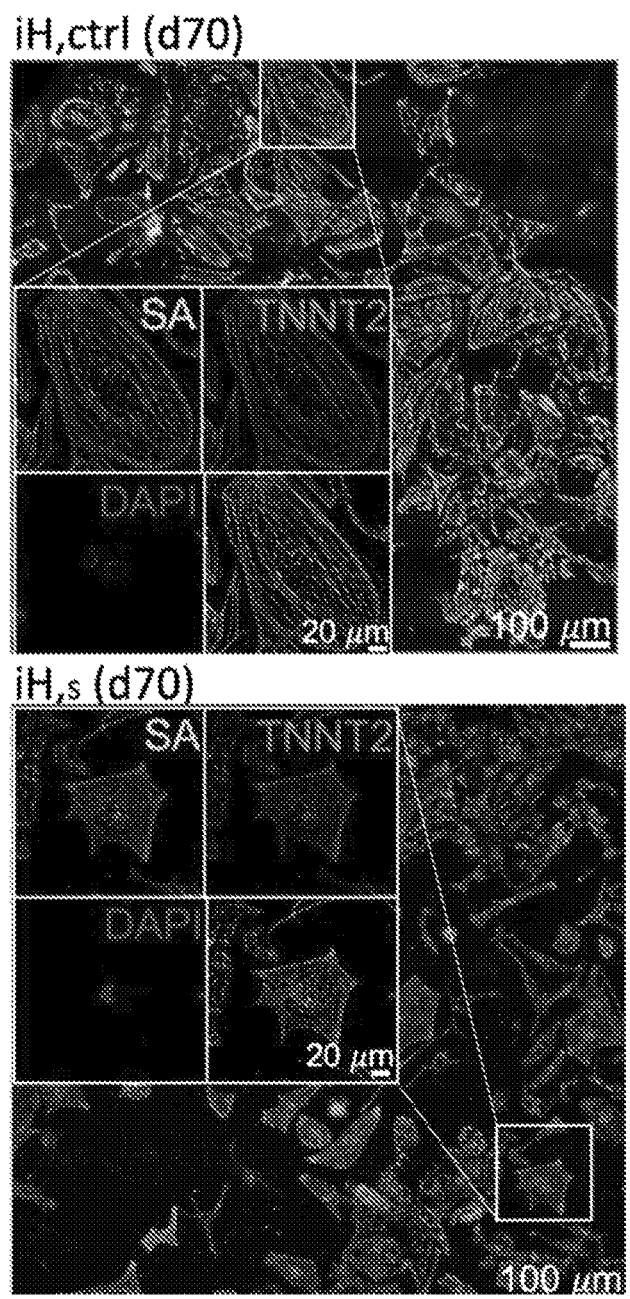
Figure 4B:
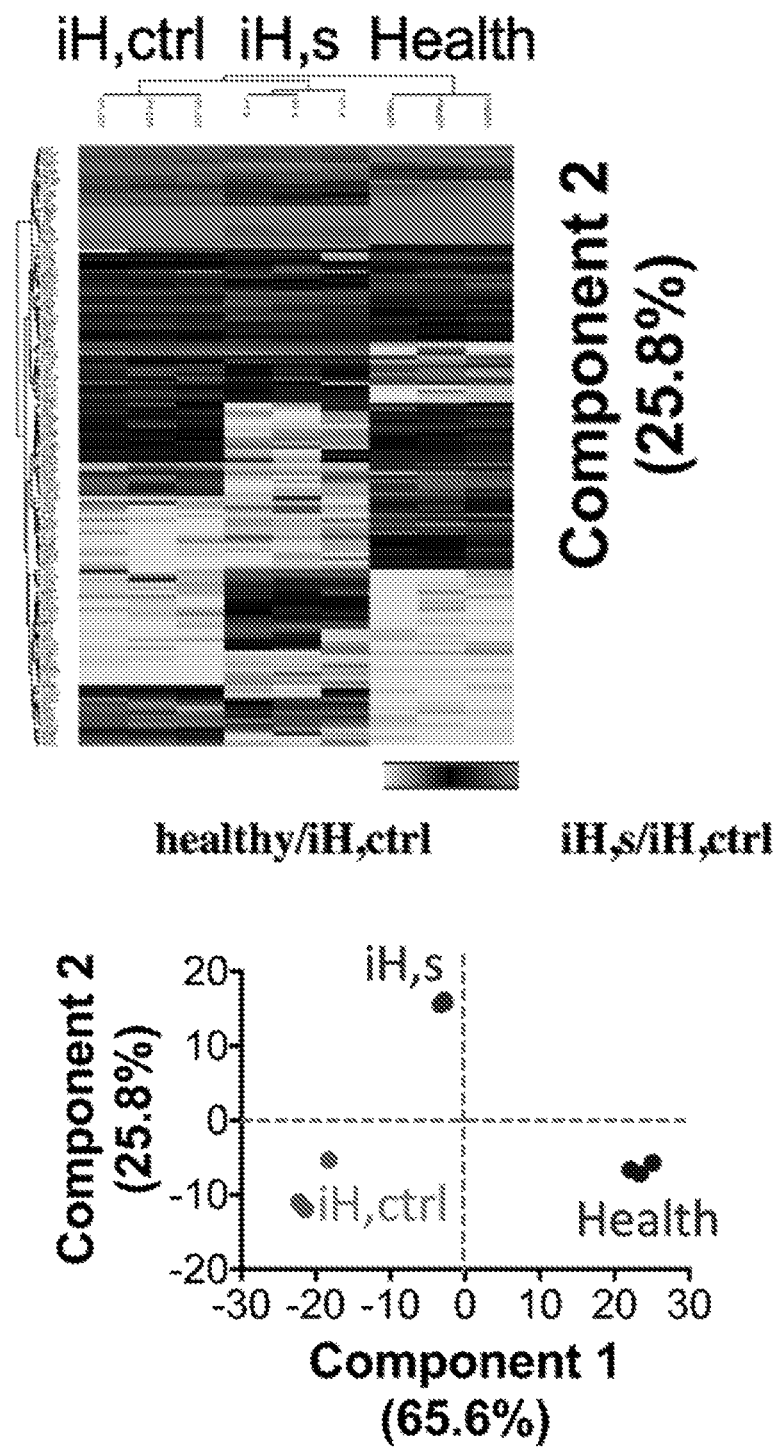
Figure 4C:
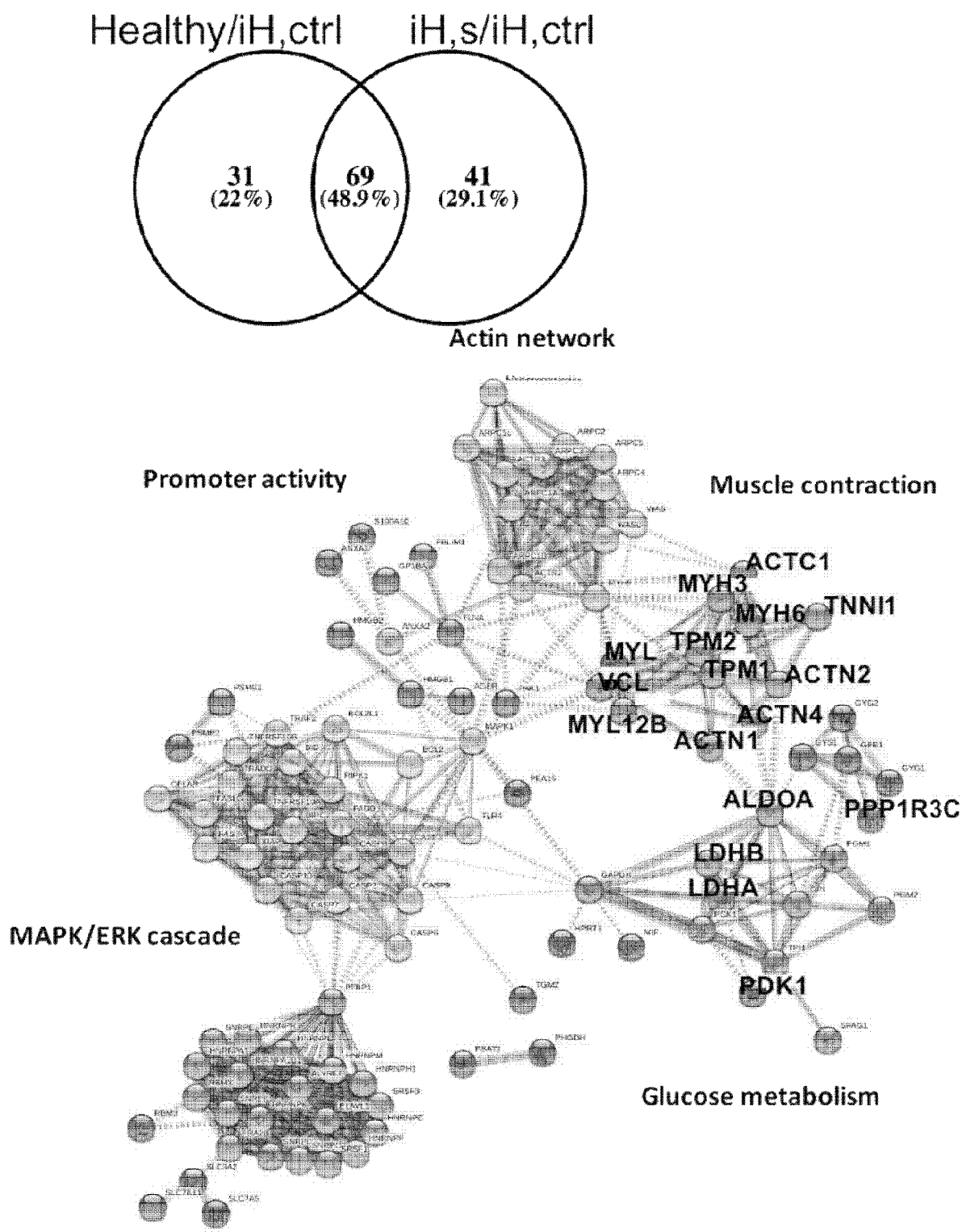
Figure 4D:
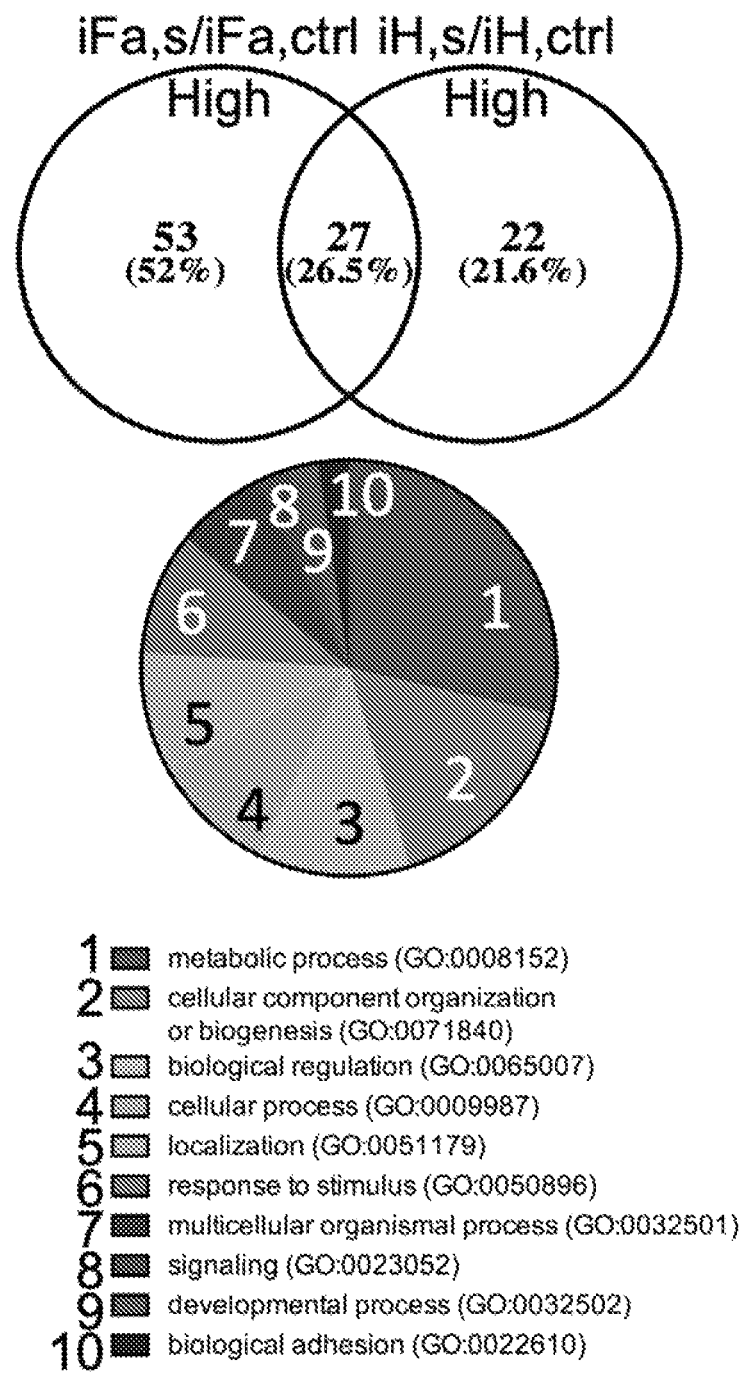

Disease modeling by human cardiomyocytes derived from the LVNC patient (iH) and the father (iFa) of the patient (iH)) induced pluripotent stem cell was performed to characterize the functional abnormalities that recapitulated the progression of cardiac dysfunction. At day 50 after differentiation in vitro, the LVNC-hiPSC-CM developed an abnormal cardiac phenotype, including the decreased myocyte contraction (FIG. 1A-B), loss of β-adrenergic responsiveness (FIG. 1C), cardiometabolic dysfunction (FIG. 1D), and abnormal omics in the functional molecules of cardiac contraction and mitochondrial respiratory chain (FIG. 1E-F). Pathway analysis predicted the abnormal epigenetic regulation might link to the abnormal metabolic process and muscular structure (FIG. 2A). Absolute quantitative real-time PCR validation found abnormal overexpression of EZH2 in LVNC cardiomyocytes (iH & iFa) (FIG. 2B). Direct EZH2 inhibitor (gsk) did not change cardiac mitochondrial dysfunction, but DNMT inhibitor (zeb) was able to recover LVNC cardiac mitochondrial function (FIG. 2C). It indicated the overexpression of EZH2 might increase the recruitment of DNMT to alter epigenetic features in LVNC myocytes and consequently led to the disturbance in the functional gene expressions. Therefore, downregulation of EZH2 expression should be a feasible therapeutic strategy to improve cardiac function in LVNC cardiomyocytes in a disease-state-specific action manner. Drug repurposing screening on this LVNC-hiPSC-CM model identified simvastatin as one capable of selectively downregulating EZH2 expression in LVNC cardiomyocytes (FIG. 3A). The beneficial effect of simvastatin was better than others (including atorvastatin, lovastatin, fluvastatin) in the recovery of cardiac contraction and β-adrenergic response after simvastatin treatment from day 30 through day 70 (FIG. 3B). Simvastatin treatment at low dose (5 μM, iH,s5 in FIG. 3C) did have better effect than treatments at high dose (10 μM, iH,s10 in FIG. 3C) in the improvement of cardiometabolic function in these LVNC-hiPSC-CMs. Simvastatin treatment was able to significantly increase the gene expressions in mitochondrial respiratory chain molecules (FIG. 3D) and cardiometabolism (FIG. 3E). Moreover, the cell size of LVNC cardiomyocytes became larger on day 70 after differentiation (FIG. 4A). Simvastatin treatment from day 30 through day 70 markedly attenuated the changes of the myocyte size (FIG. 4A). The density of either sarcomeric actinin cc or troponin T was also markedly increased in simvastatin treated cardiomyocytes. Proteomic analysis demonstrated that simvastatin was able to significantly recover the expressions of the proteins with the function of muscle contraction and metabolic process in both iH- and iFa-LVNC cardiomyocytes (FIG. 4B-D).

In Vivo Effect of Simvastatin in the Improvement of Cardiometabolism in LVNC Mice.

Drug administrations (Simvastatin: 3.5 mg/3.6 μL/kg/day; DMSO: 3.6 μL/kg/day) were conducted by the implantation of mini-osmotic pumps (ALZET model 2006, Durect Corp. Cupertino, Calif., USA) to the subcutaneous space of LVNC mice back for 6 weeks from the age of 10, 12, 14 weeks, respectively. At the endpoint, the cardiac glucose metabolic rate (MRGlu) of the fasting LVNC mice was measured. Cardiac glucose uptake of the vehicle-treated LVNC mice was gradually decreased in parallel with the deterioration of cardiac function in the elder LVNC mice (FIG. 5A). Simvastatin significantly reversed the deterioration of cardiac glucose metabolic rate occurred following the aging of LVNC mice, which demonstrated that simvastatin improved cardiac glucose metabolism in LVNC mice. Simvastatin also significantly improved cardiac contractile function (FIG. 5B). Moreover, the continuous low-dose-simvastatin treatment was needed to maintain the good prognosis of LVNC cardiac function.

Simvastatin also significantly improved mitochondrial function of LVNC cardiomyocytes derived from LVNC patients with other complications such as BS (FIG. 6A) or DMD (FIG. 6B) at dose range of 1-5 μM.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating a subject suffering from non-compaction cardiomyopathy, comprising administering to the subject suffering from non-compaction cardiomyopathy a pharmaceutical composition comprising a therapeutically effective amount of a EZH2 downregulator.

2. The method of claim 1, wherein the non-compaction cardiomyopathy comprises a left ventricle non-compaction cardiomyopathy.

3. The method of claim 1, wherein the therapeutically effective amount of the EZH2 downregulator is sufficient to treat the non-compaction cardiomyopathy by inhibiting EZH2 overexpression caused by pathogenic mutations.

4. The method of claim 1, wherein the therapeutically effective amount of the EZH2 downregulator is sufficient to treat the non-compaction cardiomyopathy by improving cardiac functions.

5. The method of claim 4, wherein the cardiac functions comprise cardiac metabolism and ventricular function.

6. The method of claim 1, wherein the EZH2 downregulator is administered to the subject daily for at least four weeks.

7. The method of claim 1, wherein the EZH2 downregulator comprises statin.

8. The method of claim 7, wherein the statin is simvastatin.

9. The method of claim 1, wherein the subject is a human.

10. The method of claim 1, wherein the therapeutically effective amount of the EZH2 downregulator ranges from 0.01 mg/kg/day to 10 mg/kg/day.

11. The method of claim 8, wherein the therapeutically effective amount of simvastatin ranges from 0.01 mg/kg/day to 10 mg/kg/day.

* * * * *